United States Patent [19]

Call

[11] Patent Number: 5,278,058
[45] Date of Patent: Jan. 11, 1994

[54] PROCESS FOR THE PRODUCTION OF LIGNOLYTICAL ENZYMES BY MEANS OF PHANEROCHAETE CHRYSOSPORIUM

[76] Inventor: Hans-Peter Call, Heinsberger Strasse 14a, D-5132 Übach-Palenberg, Fed. Rep. of Germany

[21] Appl. No.: 938,058
[22] PCT Filed: Apr. 15, 1991
[86] PCT No.: PCT/EP91/00712
§ 371 Date: Oct. 20, 1992
§ 102(e) Date: Oct. 20, 1992
[87] PCT Pub. No.: WO91/16414
PCT Pub. Date: Oct. 31, 1991

[30] Foreign Application Priority Data

Apr. 21, 1990 [DE] Fed. Rep. of Germany ....... 4012743

[51] Int. Cl.$^5$ ............... C12M 1/10; C12N 9/08
[52] U.S. Cl. ............. 435/183; 435/41; 435/71.1; 435/189; 435/192; 435/200; 435/278; 435/288
[58] Field of Search ............ 435/41, 71.1, 183, 189, 435/192, 200, 278, 288, 911

[56] References Cited

U.S. PATENT DOCUMENTS

| | | | |
|---|---|---|---|
| 4,542,101 | 9/1985 | Nees | 435/284 |
| 4,687,745 | 8/1987 | Farrell et al. | 435/189 |
| 4,889,807 | 12/1989 | Buswell et al. | 435/189 |
| 5,081,027 | 1/1992 | Nishida et al. | 435/911 |
| 5,149,648 | 9/1992 | Nishida et al. | 435/192 |
| 5,153,121 | 10/1992 | Asther et al. | 435/189 |
| 5,200,338 | 4/1993 | Crawford et al. | 435/200 |
| 5,203,964 | 4/1993 | Call | 435/278 |

FOREIGN PATENT DOCUMENTS

2934328A1 3/1981 Fed. Rep. of Germany.

OTHER PUBLICATIONS

Janshekar, H., et al., *Journal of Biotechnology*, 1988, "Cultivation of *Phanerochaete chrysosporium* and production of lignin peroxidases in submerged stirred tank reactors," 8:97–112.

Jäger, A., et al., *Applied and Environmental Microbiology*, Nov. 1985, "Production of Liginases and Degradation of Lignin in Agitated Submerged Cultures of *Phanerochaete chrysosporium*," 50(5):1274–1278.

*Primary Examiner*—Herbert J. Lilling
*Attorney, Agent, or Firm*—Feiereisen & Kueffner

[57] ABSTRACT

A process for the production of lignolytical enzymes using *Phanerochaete chrysosporium* which includes placing a culture of the pocket rot fungus *Phanerochaete chrysosporium* into a closed fermentation vessel which has no stirring mechanism. Pellets of *Phanerochaete chrysosporium* are produced in the vessel by rotating and slewing the vessel, and enzyme is then harvested. An apparatus for carrying out the process includes a cardanic mount for freely rotatably and slewably suspending the vessel.

6 Claims, 1 Drawing Sheet

PROCESS FOR THE PRODUCTION OF LIGNOLYTICAL ENZYMES BY MEANS OF PHANEROCHAETE CHRYSOSPORIUM

BACKGROUND OF THE INVENTION

1. Field of the Invention

The present invention concerns a process for the production of lignolytical enzymes by means of *Phanerochaete chrysosporium*.

2. Description of the Related Art

During the last ten years, it has been tried repeatedly to use the pocket rot fungus *Phanerochaete chrysosporium* for the production of lignolytical enzymes at industrial level. For example, there are experiments in the stirring fermenter (H. Janshekar and A. Fiechter, Journal of Biotechnology, 8 (1988), 97–112). However, these experiments were not very successful, because the pellets formed by *Phanerochaete chrysosporium* in the stirring fermenter were shattered time and again. However, since *Phanerochaete chrysosporium* only produces enzymes if it is present in pellet or immobilised form, optimal enzyme production cannot be realised in the stirring fermenter.

Moreover, biotechnology has developed reactors especially designed for sensitive cells. For example, a so-called "vibromixer" has been developed which is even suitable for sensitive animal and plant cells (Einsele, Finn, Samhaber: *Mikrobiologische und biochemische Verfahrenstechnik* (Microbiological and Biochemical Technology), Weinheim 1985, p. 150; Einsele: Chem.Ing.Tech. 45 (1973), 1368; Rehm: Chem.Ing.Tech. 42 (1970), 583). The effect of the vibromixer is based on the Bernoulli effect. Instead of the stirrer, a horizontal plate attached to a vertical shaft is positioned inside the vessel, said plate having drilled holes tapering downwards. It is moved up and down by means of the shaft. This movement causes pressure differences in the drilled holes, because the liquid in the openings flows back from the large to the small diameter. Even though the cells are moved well that way, there is practically no damage. However, such a vibromixer has the disadvantage that it still is not gentle enough for the sensitive pellets of *Phanerochaete chrysosporium*. Besides, such vibromixers cannot be used at a commercial scale to date.

Finally, glass vessels moved by mechanical shakers are also suitable for the formation of pellets of microorganisms (H.J. Rehm: *Einfuhrung in die industrielle Mikrobiologie* (Introduction into Industrial Microbiology), Berlin-Heidelberg-New York 1971). For this purpose, the vessels (mostly bottles or Erlenmeyer flasks) are clamped into the mechanical shakers in multi-stage tiers. As a result of the shaking of the vessels, air is mixed into the solution from the surface. For shaking, one uses amplitude, rotation and vibration machines which usually have variable speeds. These vessels may have planar bulges, the so-called baffle plates. The disadvantage of these systems is that they are only suitable at laboratory scale. For large-scale commercial application, thousands of bottles or Erlenmeyer flasks would be necessary, so that the use of such devices is not reasonable.

In order to solve the above-mentioned problems of using stirring reactors, scientists have increasingly tried working with immobilised cells (S. Linka, Journal of Biotechnology, 8 (1988), 163–170; H. Willershausen, A. Jäger, H. Graf, Journal of Biotechnology, 6 (1987), 239–243; Y. Linko, M. Leisola, N. Lindholm, J. Troller, P. Linko, A. Fiechter, Journal of Biotechnology 4 (1986), 283–291). However, these processes also failed at large scale. As a rule, they were no longer practicable at a fermenter volume of more than 40 l. Essentially, the reason for this can be found in the fact that *Phanerochaete chrysosporium* in pellet form has an optimal surface and thus produces enzymes best while in this state.

SUMMARY OF THE INVENTION

Therefore, it is the object of the present invention to provide a process for the production of lignolytical enzymes by means of *Phanerochaete chrysosporium* which process is also practicable in fermentation vessels of more than 40 l.

The object is solved by placing *Phanerochaete chrysosporium* into a closed vessel which does not have a stirring means and producing pellets of *Phanerochaete chrysosporium* therein by rotating and slewing said vessel; said pellets are then shaken until enzyme production takes place or are transferred to a conventional reactor immediately after the formation of the pellets in which reactor the enzyme production will then take place.

The formation of the pellets takes place in a novel reactor specially developed for the process according to the invention. This is a closed fermentation vessel which has no stirring means and which is suspended freely rotatably and slewably in a cardanic mount means. Under said vessel, there is a positioned a motor, the propeller shaft of said motor being connected to the bottom of said vessel via an eccentric.

The angle of inclination and the oscillation amplitude of said vessel can be adjusted by means of said eccentric. Thus, rotating and slewing movements of said vessel can be effected by means of the infinitely variably adjustable motor.

In the fermenter thus moved, *Phanerochaete chrysosporium* forms pellets which are not destroyed time and again by mechanical influences. As a result, the pellets obtain a shape which is optimal for enzyme production. Since, on the other hand, the oscillation of the cardanic mount of the reactor is minimal and therefore allows the construction of reactor volumes between 1 and 3 $m^3$, production of lignolytical enzymes at a commercial scale with yields hitherto considered impossible can be achieved by means of the above-described device.

It is another advantage that the pellets of *phanerochaete chrysosporium* can be reused immediately for enzyme production as soon as the enzyme production in the shaking fermenter or stirring fermenter is completed. For this purpose, it is advisable to separate the pellets from the remaining suspension and to recycle them to the stirring reactor after separation of the enzyme or to add a new substrate without a C-source (carbon source), said substrate either having a low nitrogen content or being free of nitrogen. In accordance with the invention, separation can be effected by means of ultra filtration.

Before carrying out the process according to the invention, *Phanerochaete chrysosporium* can be cultivated in a manner known per se, for example in Petri dishes or in standing cultures. The mycelia thus formed are then crushed and used in the process according to the invention.

The cultivation of *Phanerochaete chrysosporium* is carried out under conditions which are known, i.e. said cultivation generally takes place at temperatures between 37° and 40° C. and a pH value of 4.5 and 5. The preferred pH value is 5. Ventilation during the cultivation of *Phanerochaete chrysosporium* can take place continuously or intermittently. Either pure oxygen or compressed air can be used for this purpose.

BRIEF DESCRIPTION OF THE DRAWING

The single FIGURE of the drawing is a schematic elevational view of the reactor according to the present invention.

DESCRIPTION OF THE PREFERRED EMBODIMENT

Figure 1:
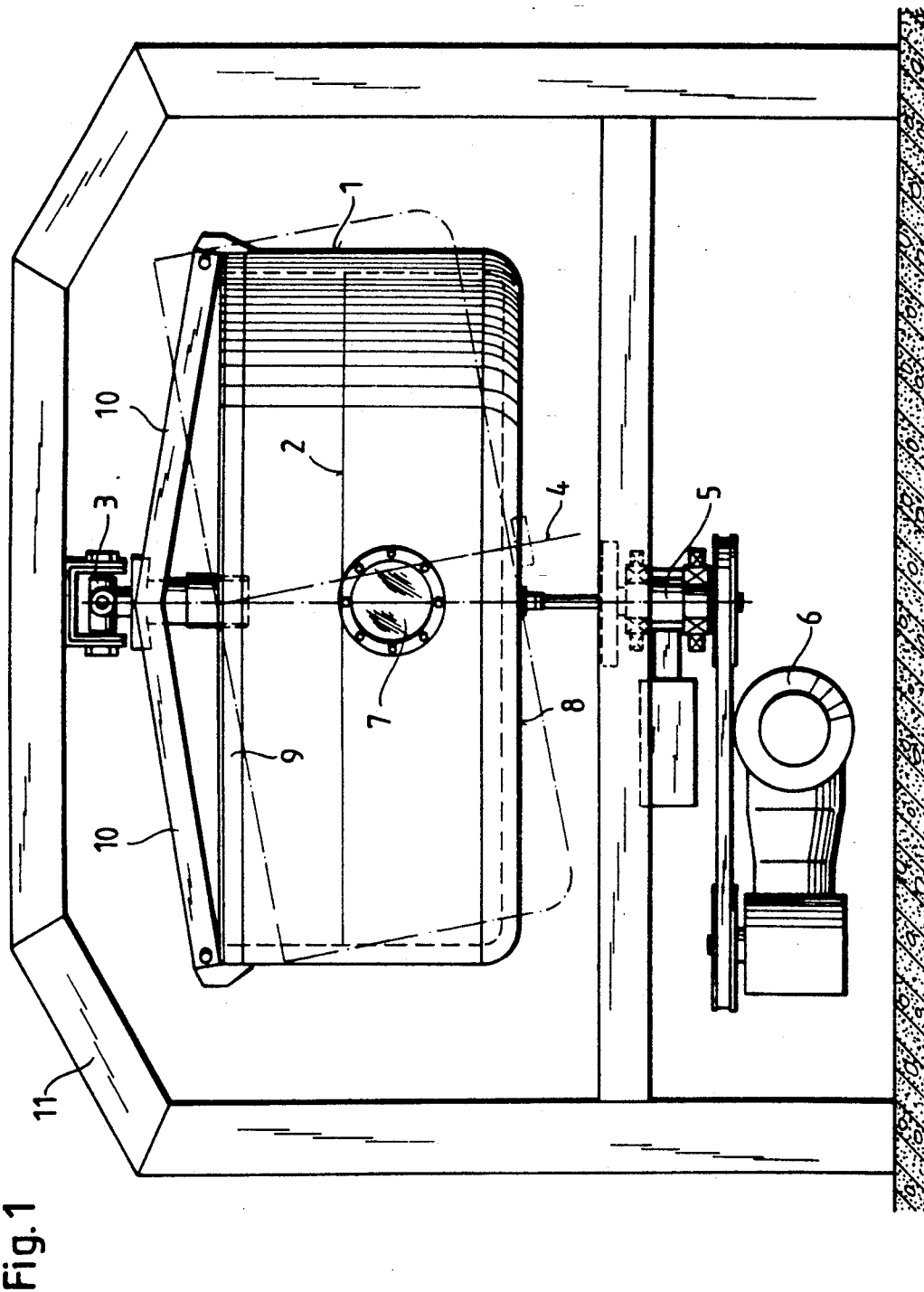

The figure shows a reactor used for the production of *Phanerochaete chrysosporium* pellets. The formation of the pellets takes place in the vessel 1. Said vessel 1 is a closed vessel having a solid bottom 8, side walls, a lid 9 and a viewing window 7. Openings for various measuring sensors ($O_2$, pH, anti-froth) as well as for feeding and withdrawing substrate and vaccination cultures are provided on the side or in the bottom. It is suspended in a frame 11 and fixed by means of the grip arms 10. Said vessel 1 is suspended freely rotatably and slewably in the cardanic mount means by means of said grip arms 10. The rotating and slewing movements are effected by the motor 6. This is connected to said bottom 8 of said vessel 1 by means of the propeller shaft 5 and the eccentric 4. The inclination and the oscillation amplitude of said vessel 1 are adjusted by means of said eccentric 4. The speed of the rotating and slewing movements of said vessel 1 is adjustable by the number of revolutions of the motor.

The invention is further illustrated by the following example:

EXAMPLE

*Phanerochaete chrysosporium* ATCC 32629 is used as strain. First, Malzagar slabs are vaccinated and then cultivated at 27° C. for approx. 10–12 days. Half of the growth is removed from these slabs, and a 50 ml standing culture is vaccinated into a 500 ml Erlenmeyer flask (cultivation time approx. 5 days at 37° C.). The pre-culture thus obtained is decanted, filled up to the original volume with a.dest. and then shredded in a Braun Starmix at stage 3 for 2×30 seconds. 15 ml of pre-culture are added per liter of medium in the shaking reactor, i.e. 75 ml would be added to a 10 l shaking reactor being filled with 5 l. The cultivation temperature is 38° C., the shaking frequency is 90 rpm and the excursion is approx. 5 cm. Each day, it is gassed with $O_2$ for 30 seconds (100 l/h). The cultivation period is 4–5 days. The enzyme harvest is approx. 50–100 U/l (1 U=1 μmole turnover of veratryl alcohol to veratryl aldehyde/min.) A maximum of 10 U/l can be achieved under the same conditions in a conventional stirring reactor.

The media are composed as follows:
Pre-culture medium:

1) Mineral salt solution (ME): (per liter) 10.5 g nitrilo triacetate; 21 g $MgSO_4$, 3.5 g $MnSO_4$; 7 g NaCl, 0.7 g $FeSO_4$; 0.7 g $CoCl_2$; 0.7 g $CaCl_2$; 0.7 g $ZnSo_4$; 0.07 g $CuSO_4$, 0.07 g $AlK_2SO_4$; 0.07 g $H_3BO_3$; 0.07 g $NaMoO_4$.

2) Solution 1 (salt solution) (per liter) 20 g $KH_2PO_4$; 5 g $MgSO_4$; 1 g $CaCl_2$.

3) Buffer (pH 4.5–5.5)
1 m $NaH_2PO_4/NaH_2PO_4$-buffer
Composition per 1 l of medium:
0.2 g ammonium tartrate
100 ml solution 1
1.43 ml ME solution
10 g glucose
10 ml buffer
+0.9 ml thiamine 100 mg/l (is added in sterilely filtered form after treatment in the autoclave)
Main culture medium:
Composition per 1 medium:
0.2 g ammonium tartrate
100 ml solution 1
10 ml ME solution
10 g glucose
10 ml buffer
67.3 mg veratryl alcohol
2 ml Tween 80
+0.9 ml thiamine (100 mg/1)

I claim:
1. A process for the production of lignolytical enzymes by means of *Phanerochaete chrysosporium* in a closed vessel without stirring means, the vessel being suspended freely rotatably and slewably in a cardanic mount means, a motor being positioned under a floor of the vessel, the motor having a propeller shaft, wherein an excentric connects the propeller shaft to the floor of the vessel, comprising
   a) producing a culture of the pocket rot fungus *Phanerochaete chrysosporium* in the closed vessel (1);
   b) producing pellets of *Phanerochaete chrysosporium* by rotating and slewing said vessel (1); and
   c) subsequently harvesting the enzyme.

2. A process according to claim 1, comprising transferring the suspension containing the pellets into a conventional stirring reactor before the enzyme harvest and producing the enzymes in the stirring reactor by means of the pellets.

3. An apparatus operating without stirring means for producing pellets of the fungus *Phanerochaete chrysosporium*, the apparatus comprising a closed fermentation vessel (1) which is suspended freely rotatably and slewably in a cardanic mount means (3), a motor (6) positioned under a floor (8) of said vessel (1), said motor (6) having a propeller shaft (5), further comprising an excentric (4) connecting the propeller shaft (5), further comprising an excentric (4) connecting the propeller shaft (5) of said motor (6) to said floor (8) of said vessel (1).

4. An apparatus according to claim 3, comprising means for infinitely variably adjusting a rotating speed of said motor.

5. An apparatus according to claim 3, wherein said excentric comprises means for adjusting an angle of inclination and an oscillation amplitude of said vessel (1).

6. A process according to claim 1, comprising aerating the culture with oxygen or compressed air.

* * * * *